(12) United States Patent
Worthen et al.

(10) Patent No.: US 10,144,356 B2
(45) Date of Patent: Dec. 4, 2018

(54) CONDENSATION DETECTION FOR VEHICLE SURFACES VIA LIGHT TRANSMITTERS AND RECEIVERS

(71) Applicant: Ford Global Technologies, LLC, Dearborn, MI (US)

(72) Inventors: Reid William Kaufman Worthen, Dearborn, MI (US); Victoria Leigh Schein, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/469,270

(22) Filed: Mar. 24, 2017

(65) Prior Publication Data
US 2018/0272946 A1    Sep. 27, 2018

(51) Int. Cl.
| | |
|---|---|
| *B60R 1/06* | (2006.01) |
| *B60R 1/12* | (2006.01) |
| *G01D 5/34* | (2006.01) |
| *B60R 1/08* | (2006.01) |
| *G01N 21/47* | (2006.01) |

(52) U.S. Cl.
CPC ............... *B60R 1/12* (2013.01); *B60R 1/06* (2013.01); *B60R 1/0602* (2013.01); *B60R 1/088* (2013.01); *G01D 5/34* (2013.01); *G01N 21/47* (2013.01); *B60R 2001/1223* (2013.01)

(58) Field of Classification Search
CPC ......... B60R 1/12; B60R 1/0602; B60R 1/088; B60R 2001/1223; B60R 1/06; G01D 5/34; G01N 21/47

USPC .......................................................... 359/275
See application file for complete search history.

(56) References Cited

U.S. PATENT DOCUMENTS

| | | |
|---|---|---|
| 4,439,021 A | 3/1984 | Gross |
| 4,572,619 A | 2/1986 | Reininger |
| 4,690,508 A | 9/1987 | Jacob |
| 4,697,883 A | 10/1987 | Suzuki |
| 4,871,917 A * | 10/1989 | O'Farrell ............. B60S 1/0822 15/DIG. 15 |

(Continued)

FOREIGN PATENT DOCUMENTS

| | | |
|---|---|---|
| CN | 103481825 A | 1/2014 |
| CN | 206012464 U | 3/2017 |

(Continued)

OTHER PUBLICATIONS

Windshield Wiper Problems; Jan. 30, 2017; AGCO Automotive Corporation , https://www.agcauto.com/.

(Continued)

*Primary Examiner* — William R Alexander
(74) *Attorney, Agent, or Firm* — James P. Muraff; Neal, Gerber & Eisenberg LLP

(57) ABSTRACT

Method and apparatus are disclosed for condensation detection for vehicle surfaces via light transmitters and receivers. An example vehicle includes a side mirror including a front surface and a back surface, a light transmitter adjacent to the front surface for emitting a light beam toward the side mirror, a first light sensor adjacent to the back surface for detecting a first light intensity of the light beam, and an opaqueness detector that determines whether condensation is on the side mirror based upon the first light intensity.

19 Claims, 7 Drawing Sheets

(56) References Cited

U.S. PATENT DOCUMENTS

| | | | |
|---|---|---|---|
| 4,970,122 A * | 11/1990 | Palanisamy | B60S 1/0822 296/84.1 |
| 5,446,586 A | 8/1995 | Dornier | |
| 5,821,501 A * | 10/1998 | Zorn | B60R 1/0602 219/202 |
| 5,898,193 A | 4/1999 | Teder | |
| 6,262,407 B1 | 7/2001 | Teder | |
| 6,307,198 B1 * | 10/2001 | Asakura | B32B 17/10036 250/227.25 |
| 6,555,804 B1 | 4/2003 | Biasing | |
| 6,674,370 B2 | 1/2004 | Rodewald et al. | |
| 6,853,897 B2 | 2/2005 | Stam et al. | |
| 7,006,129 B1 | 2/2006 | McClure | |
| 7,184,074 B1 | 2/2007 | Jansen | |
| 7,253,898 B2 | 8/2007 | Saikalis | |
| 7,385,216 B2 | 6/2008 | Yoshigoe | |
| 7,420,671 B2 | 9/2008 | Sonda | |
| 7,847,255 B2 | 12/2010 | Teder | |
| 8,334,972 B2 | 12/2012 | Thien | |
| 8,344,288 B2 * | 1/2013 | Door | H05B 3/845 219/202 |
| 9,120,464 B2 | 9/2015 | Pack et al. | |
| 2002/0040964 A1 * | 4/2002 | Dausmann | B60S 1/0822 250/227.25 |
| 2003/0016125 A1 | 1/2003 | Lang | |
| 2005/0040151 A1 * | 2/2005 | Dyrdek | H05B 3/84 219/203 |
| 2005/0174561 A1 * | 8/2005 | Murakami | B32B 17/10036 356/37 |
| 2006/0016097 A1 * | 1/2006 | Chiang | F25D 21/08 34/549 |
| 2006/0016795 A1 * | 1/2006 | Witzke | B60R 1/0602 219/219 |
| 2008/0037130 A1 | 2/2008 | Turnbull | |
| 2009/0161109 A1 * | 6/2009 | Wolf | B60S 1/0822 356/445 |
| 2009/0315723 A1 * | 12/2009 | Linsenmaier | B60R 1/0602 340/583 |
| 2011/0168687 A1 * | 7/2011 | Door | B60R 1/0602 219/202 |
| 2016/0119586 A1 | 4/2016 | Riad et al. | |
| 2017/0115235 A1 | 4/2017 | Ohlsson | |
| 2018/0022320 A1 * | 1/2018 | Lee | B60S 1/0825 |

FOREIGN PATENT DOCUMENTS

| | | |
|---|---|---|
| CN | 107458313 A | 12/2017 |
| DE | 3823909 A1 | 7/1974 |
| DE | 3328652 A1 | 2/1985 |
| DE | 3721659 A1 | 1/1989 |
| DE | 102004047215 A1 | 4/2006 |
| DE | 102005027087 A1 | 12/2006 |
| DE | 102007002257 A1 | 7/2008 |
| DE | 102008054640 A1 | 6/2010 |
| EP | 0919443 A2 | 2/1999 |
| JP | 2000127850 A | 5/2000 |
| JP | 2008185531 A | 4/2008 |
| KR | 20080061620 A | 7/2008 |
| KR | 20160115117 A | 4/2016 |
| WO | WO 2001/031319 A1 | 5/2001 |
| WO | WO 2014/051335 A1 | 4/2014 |
| WO | WO 2014130049 A1 | 8/2014 |
| WO | WO 2015162322 A1 | 10/2015 |

OTHER PUBLICATIONS

Search Report dated Sep. 13, 2018 for GB Patent Application No. 1804495.8 (5 pages).

Search Report dated Sep. 13, 2018 for GB Patent Application No. 18044493.3 (5 pages).

Search Report dated Sep. 19, 2018 for GB Patent Application No. 1804492.5 (5 pages).

* cited by examiner

CONDENSATION DETECTION FOR VEHICLE SURFACES VIA LIGHT TRANSMITTERS AND RECEIVERS

CROSS-REFERENCE TO RELATED APPLICATIONS

This application relates to U.S. application Ser. No. 15/469,256 filed on Mar. 24, 2017 and U.S. application Ser. No. 15/469,239 filed on Mar. 24, 2017, both of which are incorporated by reference in their entireties.

TECHNICAL FIELD

The present disclosure generally relates to condensation and, more specifically, to condensation detection for vehicle surfaces via light transmitters and receivers.

BACKGROUND

Generally, a vehicle includes a windshield, a rear window, and side windows that partially define a cabin of the vehicle and enable a driver and/or other occupant(s) (e.g., passengers) to view an area surrounding the vehicle. Oftentimes, the windshield is formed from laminated safety glass, and the side and rear windows are formed from tempered glass, laminated glass, polycarbonate, acrylic resins, and/or other materials.

A vehicle also typically includes mirrors (e.g., a rearview mirror, side mirrors) to facilitate a driver in viewing a surrounding area next to and/or behind the vehicle. Oftentimes, the mirrors of the vehicle include a reflective layer (e.g., formed of metallic material) and a glass or plastic layer coupled to the reflective layer to protect the reflective layer from becoming damaged.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

Example embodiments are shown for condensation detection for vehicle surfaces via light transmitters and receivers. An example disclosed vehicle includes a side mirror including a front surface and a back surface, a light transmitter adjacent to the front surface for emitting a light beam toward the side mirror, a first light sensor adjacent to the back surface for detecting a first light intensity of the light beam, and an opaqueness detector that determines whether condensation is on the side mirror based upon the first light intensity.

An example disclosed method for detecting condensation on vehicle mirrors includes emitting a light beam toward a side mirror of a vehicle via a light transmitter adjacent a front surface of the side mirror and detecting a first light intensity of the light beam via a first light sensor adjacent a back surface of the side mirror. The example disclosed method also includes determining, via a processor, whether condensation is on the side mirror based upon the first light intensity.

BRIEF DESCRIPTION OF THE DRAWINGS

For a better understanding of the invention, reference may be made to embodiments shown in the following drawings.

The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION OF EXAMPLE EMBODIMENTS

Figure 1:
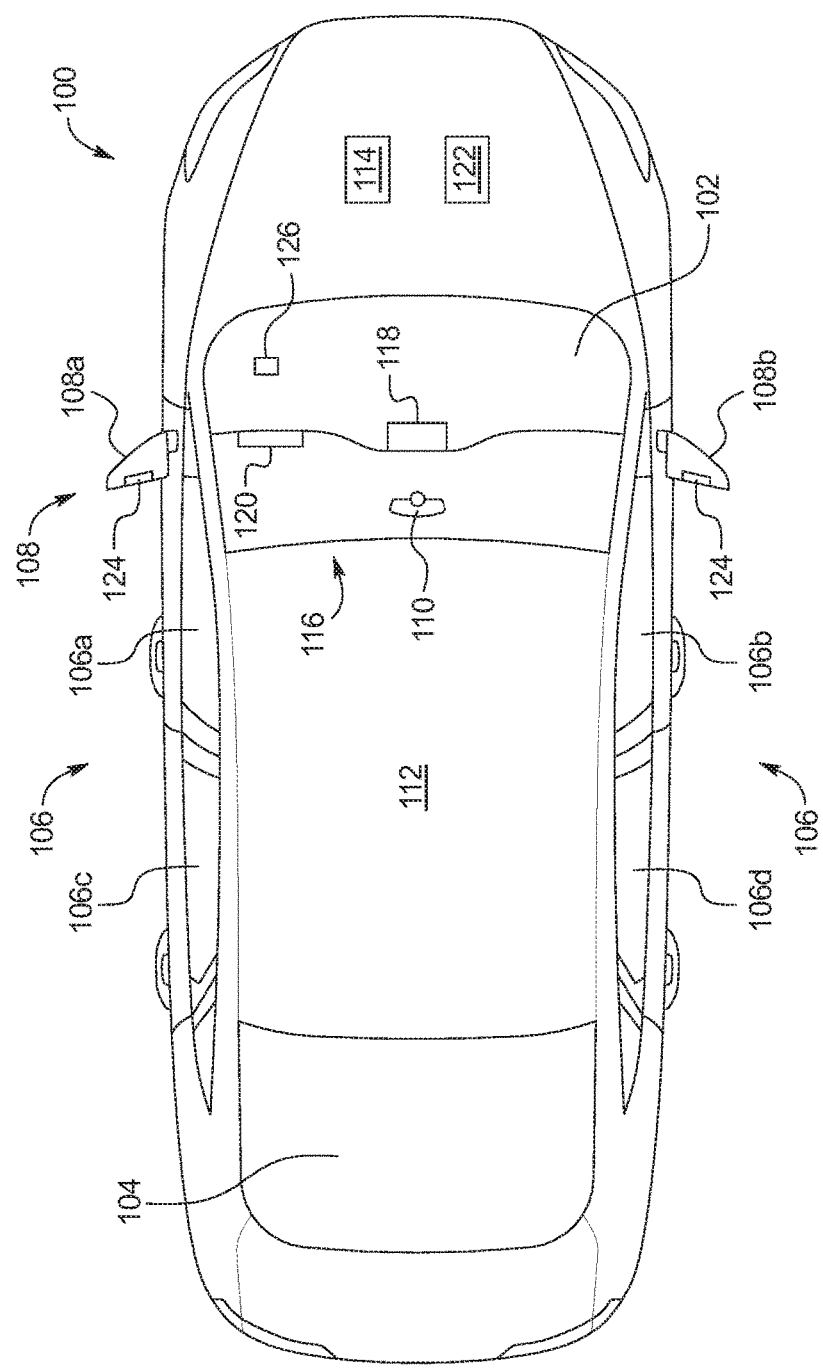
FIG. 1 illustrates an example vehicle in accordance with the teachings disclosed herein.

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

Generally, a vehicle includes a windshield, a rear window, and side windows that partially define a cabin of the vehicle and enable a driver and/or other occupant(s) (e.g., passengers) to view an area surrounding the vehicle. Oftentimes, the windshield is formed from laminated safety glass, and the side and rear windows are formed from tempered glass, laminated glass, polycarbonate, acrylic resins, and/or other materials.

Further, a vehicle typically includes a rearview mirror and side mirrors (i.e., side-view mirrors, wing mirrors, fender mirrors) to facilitate a driver in viewing a surrounding area next to and/or behind the vehicle. Oftentimes, rearview mirrors and side mirrors include a reflective layer (e.g., formed of aluminum and/or other metallic material(s)) and a glass or plastic layer coupled to the reflective layer to protect the reflective layer from becoming damaged.

In some instances when a glass temperature is at or below a dew point temperature, a film of condensation and/or ice forms on one or more windows and/or mirrors as a result of condensation collecting on a surface of the window(s) and/or mirror(s). For example, condensation collects on a side mirror when a temperature of a glass layer of the side mirror is at or below a dew point temperature of air adjacent to the glass layer. Similarly, condensation collects on a window when a temperature of the window is at or below a dew point temperature of air adjacent to the window. In other instances, condensation collects on a side window that originates, at least in part, from moisture expelled by a vehicle occupant breathing, wet clothing, water and/or snow brought into the vehicle, etc. When mirror(s) and/or adjacent window(s) of a vehicle become opaque due to condensation, ice, rain droplets, snow, dirt, cracked glass surfaces, etc., it potentially may be become difficult for a driver of the vehicle to view the surrounding area of the vehicle.

Example apparatus, methods, and computer readable media disclosed herein include light sensors of a vehicle that detect when opaque material is located on a mirror and/or an adjacent window of the vehicle to facilitate a driver of the vehicle in viewing a surrounding area via the mirror and/or through the window.

In some examples disclosed herein, the vehicle includes one or more front sensors adjacent a front surface of a mirror (e.g., a side mirror, a rearview mirror) collect a first ambient light intensity and one or more back sensors adjacent a back surface of the mirror collect a second ambient light intensity. An opaqueness detector detects whether condensation and/or other opaque material is on the mirror based upon comparing the first ambient light intensity and the second ambient light intensity.

Additionally, in some examples disclosed herein, the vehicle includes a light transmitter adjacent to the front surface of the mirror that emits a light beam toward the mirror and one or more light sensors (e.g., a first light sensor) adjacent to the back surface that detect a first light intensity of the light beam. The opaqueness detector determines whether condensation and/or other opaque material is on the side mirror based upon a comparison of the first light intensity to a reference light intensity.

In some examples disclosed herein, the vehicle includes one or more cabin sensors adjacent an interior surface of a window (e.g., a windshield, a rear window, a side window adjacent a side mirror) collect a first ambient light intensity and one or more exterior sensors adjacent a exterior surface of the window collect a second ambient light intensity. The opaqueness detector detects whether condensation and/or other opaque material is on the window based upon comparing the first ambient light intensity and the second ambient light intensity.

Also, in some examples disclosed herein, the vehicle includes a light transmitter adjacent to a first surface (e.g., the interior surface) of the window that emits a light beam toward the window and one or more light sensors (e.g., a first light sensor) adjacent to a second surface (e.g., the exterior surface) of the window that detect a first light intensity of the light beam. The opaqueness detector determines whether condensation and/or other opaque material is on the window based upon a comparison of the first light intensity to a reference light intensity.

Regarding the figures, FIG. 1 illustrates an example vehicle 100 in accordance with the teachings disclosed herein. The vehicle 100 may be a standard gasoline powered vehicle, a hybrid vehicle, an electric vehicle, a fuel cell vehicle, and/or any other mobility implement type of vehicle. The vehicle 100 includes parts related to mobility, such as a powertrain with an engine, a transmission, a suspension, a driveshaft, and/or wheels, etc. The vehicle 100 may be non-autonomous, semi-autonomous (e.g., some routine motive functions controlled by the vehicle 100), or autonomous (e.g., motive functions are controlled by the vehicle 100 without direct driver input).

In the illustrated example, the vehicle 100 includes a windshield 102, a rearview window 104, side windows 106, side mirrors 108, and a rearview mirror 110. For example, the windshield 102 is formed from laminated safety glass, and the rearview window 104 and side windows 106 are formed from tempered glass, laminated glass, polycarbonate, acrylic resins, and/or other materials. In the illustrated example, the side windows 106 include a side window 106a (e.g., a first side window, a front driver-side window), a side window 106b (e.g., a second side window, a front passenger-side window), a side window 106c (e.g., a third side window, a rear driver-side window), and a side window 106d (e.g., a fourth side window, a rear passenger-side window). Further the side mirrors 108 include a side mirror 108a (e.g., a first side mirror, a driver-side side mirror) and a side mirror 108b (e.g., a second side mirror, a passenger-side side mirror).

Further, the vehicle 100 of the illustrated example includes a cabin 112 and an HVAC system 114. The HVAC system 114 adjusts, maintains, and/or otherwise affects an environment within the cabin 112 of the vehicle 100. For example, the HVAC system 114 includes vents, a heater, and/or an air conditioner to control a temperature and/or a moisture level within the cabin 112 of the vehicle 100.

The vehicle 100 also includes an infotainment head unit 116 provides an interface between the vehicle 100 and a user. The infotainment head unit 116 includes digital and/or analog interfaces (e.g., input devices and output devices) to receive input from and display information for the user(s). The input devices include, for example, a control knob, an instrument panel, a digital camera for image capture and/or visual command recognition, a touch screen, an audio input device (e.g., cabin microphone), buttons, or a touchpad. The output devices may include instrument cluster outputs (e.g., dials, lighting devices), actuators, a display 118 (e.g., a heads-up display, a center console display such as a liquid crystal display (LCD), an organic light emitting diode (OLED) display, a flat panel display, a solid state display, etc.), and/or speakers 120. In the illustrated example, the infotainment head unit 116 includes hardware (e.g., a processor or controller, memory, storage, etc.) and software (e.g., an operating system, etc.) for an infotainment system (such as SYNC® and MyFord Touch® by Ford®, Entune® by Toyota®, IntelliLink® by GMC®, etc.). Additionally, the infotainment head unit 116 displays the infotainment system on, for example, the display 118.

In the illustrated example, the display 118 presents an audio alarm and/or the speakers 120 present a visual alarm in response an opaqueness detector 122 of the vehicle 100 detecting that condensation, rain, snow, ice, and/or other opaque materials (e.g., broken glass) on and/or of the windshield 102, the rearview window 104, one or more of the side windows 106, one or more of the side mirrors 108, and/or the rearview mirror 110 of the vehicle 100. As illustrated in FIG. 1, the vehicle 100 includes an opaqueness detection assembly 124 for each of the side mirrors 108 and an opaqueness detection assembly 126 for the windshield 102. The opaqueness detection assembly 124 and the opaqueness detection assembly 126 collect or receive light intensity measurements or data to enable the opaqueness detector 122 to determine whether opaque material(s) are located on the respective surfaces of the vehicle 100. In some examples, the vehicle 100 includes another opaqueness detection assembly identical or substantially similar to the opaqueness detection assembly 124 for the rearview mirror 110. Additionally or alternatively, the vehicle 100 includes other opaqueness detection assemblies identical or substantially similar to the opaqueness detection assembly 126 for the rearview window 104 and/or one or more of the side windows 106 to enable the opaqueness detector 122 to detect opaque material(s) on the rearview window 104 and/or the one or more of the side windows 106.

Figure 2:
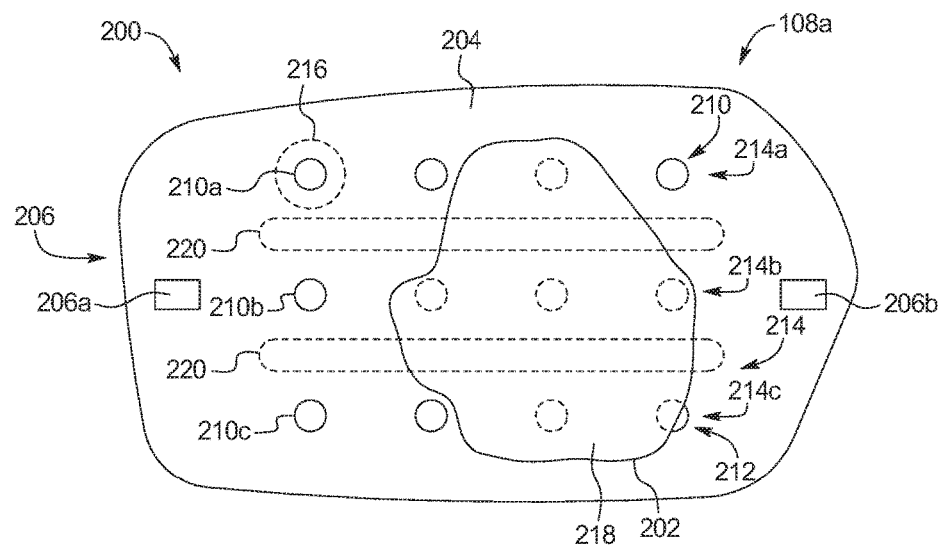
FIG. 2 illustrates a side window of the vehicle of FIG. 1 and an example opaqueness detection assembly in accordance with the teachings disclosed herein.

FIG. 2 illustrates an example opaqueness detection assembly 200 (e.g., the opaqueness detection assembly 124) that is utilized to detect whether opaque material 202 has collected on or formed in a front surface 204 of the side mirror 108a in accordance with the teachings disclosed herein. Additionally or alternatively, the opaqueness detection assembly 200 may be utilized for detecting the opaque material 202 on the side mirror 108b. Further, features of the side mirror 108a are discussed in detail with respect to FIGS. 2 and 3. Because the side mirror 108b is identical or substantially similar to the side mirror 108a, some features of the side mirror 108b will not be discussed in further detail below.

As illustrated in FIG. 2, the opaqueness detection assembly 200 includes front sensors 206 (e.g., reference sensors) located adjacent to the front surface 204 of the side mirror 108a. In the illustrated example, the front sensors 206 include a front sensor 206a (e.g., a first front sensor) and a front sensor 206b (e.g., a second font sensor). The front sensors 206 are positioned adjacent to the front surface 204 near an edge 208 of the side mirror 108a to deter the front sensors 206 from obstructing a driver's view of an area surrounding the vehicle 100 via the side mirror 108a. Further, the opaqueness detection assembly 200 includes a plurality of back sensors 210 that are located adjacent to a back surface (e.g., a back surface 306 of FIG. 3) of the side mirror 108a. In the illustrated example, the back sensors 210 form a sensor matrix 212 that includes a plurality of sensor arrays 214. The sensor arrays 214 include a sensor array 214a (e.g., a first sensor array), a sensor array 214b (e.g., a second sensor array), and a sensor array 214c (e.g., a first sensor array). Each of the sensor arrays 214 are adjacent to the back surface of the side mirror 108a and include a plurality of the back sensors 210. For example, the sensor array 214a includes a back sensor 210a (e.g., a first back sensor), the sensor array 214b includes a back sensor 210b (e.g., a second back sensor), and the sensor array 214c includes a back sensor 210c (e.g., a third back sensor).

In the illustrated example, the front sensors 206 and the back sensors 210 collect ambient light measurements to enable the opaqueness detector 122 to detect whether condensation, rain droplets, snow, ice, dirt and/or other opaque materials have collected on the front surface 204 of the side mirror 108a. Additionally or alternatively, the front sensors 206 and the back sensors 210 collect ambient light measurements to enable the opaqueness detector 122 to detect whether cracks have formed in the side mirror 108a of the vehicle 100. The opaqueness detector 122 compares ambient light measurements collected by the front sensors 206 along the front surface 204 of the side mirror 108a to ambient light measurements collected by the back sensors 210 along the back surface of the side mirror 108a to determine whether opaque material has collected on the front surface 204 of the side mirror 108a. That is, the opaqueness detector 122 compares the light intensity in front of the side mirror 108a to the light intensity behind the side mirror 108a to determine whether opaque material has caused the side mirror 108a to be at least partially unreflective.

For example, the front sensor 206a collects an ambient light intensity (e.g., a first ambient light intensity) and the back sensor 210a collects an ambient light intensity (e.g., a second ambient light intensity). The opaqueness detector 122 compares the first ambient light intensity and the second ambient light intensity to determine whether condensation and/or other opaque material has collected on the front surface 204 in an area 216 around the back sensor 210a. For example, the opaqueness detector 122 detects that condensation has formed on the side mirror 108a in the area 216 around the back sensor 210a when the second ambient light intensity measured by the back sensor 210a is less than the first ambient light intensity by a first predetermined value that corresponds to a layer of condensation on the front surface 204. That is, condensation that collects on the front surface 204 between the back sensor 210a and the front sensor 206a causes the back sensor 210a to measure less light intensity than the front sensor 206a by the first predetermined value. Further, the front sensor 206b of the illustrated example collects an ambient light intensity (e.g., a third ambient light intensity). The opaqueness detector 122 further detects whether condensation and/or other opaque material has collected on the front surface 204 in an area 216 around the back sensor 210a by comparing the first ambient light intensity collected by the back sensor 210a to the third ambient light intensity collected by the front sensor 206b.

In some examples, the opaqueness detection assembly 200 enables the opaqueness detector 122 to determine which type of material is forming an opaque surface on the side mirror 108a. For example, when the second ambient light intensity measured by the back sensor 210a is less than the first ambient light intensity measured by the front sensor 206a by the first predetermined value, the opaqueness detector 122 detects that condensation is on the side mirror 108a in the area 216 around the back sensor 210a. When the second ambient light intensity is less than the first ambient light intensity by a second predetermined value, the opaqueness detector 122 detects that rain droplets are on the side mirror 108a in the area 216 around the back sensor 210a. When the second ambient light intensity is less than the first ambient light intensity by a third predetermined value, the opaqueness detector 122 detects that snow is on the side mirror 108a in the area 216 around the back sensor 210a. Further, when the second ambient light intensity is less than the first ambient light intensity by a fourth predetermined value, the opaqueness detector 122 detects that ice is on the side mirror 108a in the area 216 around the back sensor 210a.

The opaqueness detection assembly 200 of the illustrated example also enables the opaqueness detector 122 to determine a location 218 of the opaque material 202 on the side mirror 108a. For example, the front sensors 206 and the back sensors 210 are utilized to determine that the opaque material 202 covers a center portion of the side mirror 108a by identifying which of the back sensors 210 collect ambient light intensity that is affected by the opaque material 202 and which of the back sensors 210 collect light intensity that is not affected by the opaque material 202. Further, in some examples, the opaqueness detector 122 presents an alarm (e.g., via the display 118 and/or the speakers 120) upon detecting the opaque material 202 (e.g., condensation) on the side mirror 108a. Additionally or alternatively, the opaqueness detector 122 activates one or more mirror heating elements 220 upon detecting the opaque material 202 (e.g., condensation) on the side mirror 108a to melt the opaque material 202 off the side mirror 108a.

Figures 3, 4:
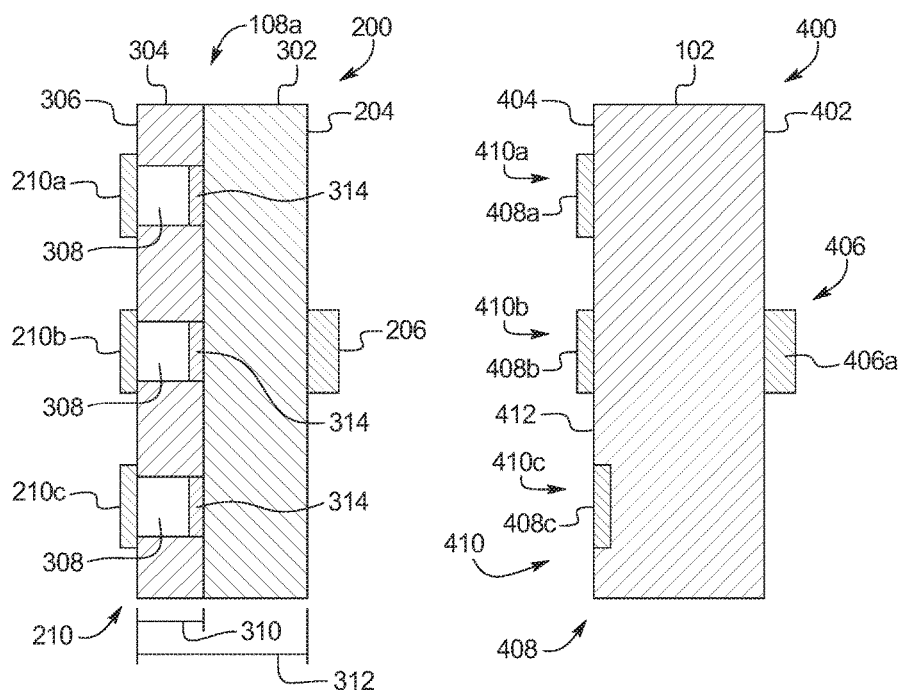
FIG. 3 depicts a cross-sectional diagram of the side window and the opaqueness detection assembly of FIG. 2.
FIG. 4 depicts a cross-sectional diagram of a window of the vehicle of FIG. 1 and the opaqueness detection assembly of FIG. 2.

FIG. 3 depicts a cross-sectional diagram of the side mirror 108a and the opaqueness detection assembly 200. As illustrated in FIG. 3, the side mirror 108a includes a glass layer 302 that defines the front surface 204 and a reflective layer 304 that defines a back surface 306 of the side mirror 108a. For example, the reflective layer 304 is formed of aluminum and/or any other metallic material that reflects images. The glass layer 302 forms a protective layer to deter the reflective layer 304 from being damaged. Further, while the side mirror 108a of the illustrated includes the glass layer 302, the side mirror 108a in other examples may include a layer of plastic and/or any other clear, protective material.

In the illustrated example, the front sensors 206 are coupled to the front surface 204, and the back sensors 210 are coupled to the back surface 306 to securely position the front sensors 206 and the back sensors 210. Further, the front sensors 206 and the back sensors 210 are coupled to the front surface 204 and the back surface 306, respectively, to prevent material from being positioned between the front sensors 206 and/or the back sensors 210 and the side mirror 108a. For example, the front sensors 206 and/or the back sensors 210 may be coupled to the side mirror 108a via a bracket and/or adhesive. In other examples, the front sensors 206 may be spaced apart from the front surface 204 and/or the back sensors 210 may be spaced apart from the back surface 306.

As illustrated in FIG. 3, the side mirror 108a includes one or more apertures 308 that extend through a thickness 310 of the reflective layer 304 such that the apertures 308 extend through at least a portion of a thickness 312 of the side mirror 108a. Each of the back sensors 210 (e.g., the back sensor 210a) is adjacent to a corresponding one of the apertures 308 to enable each of the back sensors 210 to collect a measurement of ambient light intensity (e.g., the second ambient light intensity). Further, in the illustrated example, each of the apertures 308 is covered with an electrochromic material layer 314 that camouflages the apertures 308 with the front surface 204 of the side mirror 108a when an electric charge is applied to the electrochromic material layer 314.

FIG. 4 depicts a cross-sectional diagram of an opaqueness detection assembly 400 that facilitates detection of opaque materials located on a window of the vehicle 100. In the illustrated example, the opaqueness detection assembly 200 (e.g., the opaqueness detection assembly 126) is utilized to monitor the windshield 102. Additionally or alternatively, the opaqueness detection assembly 400 is utilized to monitor one or more of the side windows 106 and/or the rearview window 104 of the vehicle 100.

In the illustrated example, the windshield 102 includes a first surface 402 (e.g., an interior surface) and a second surface 404 (e.g., an exterior surface). Further, the opaqueness detection assembly 400 includes cabin sensors 406 (e.g., reference sensors) that are located adjacent to the first surface 402. For example, the cabin sensors 406 include a first cabin sensor 406a, a second cabin sensor, etc. Further, the opaqueness detection assembly 400 includes a plurality of exterior sensors 408 that are located adjacent to the second surface 404. The exterior sensors 408 form a sensor matrix that includes sensor arrays 410. The sensors arrays include a sensor array 410a (e.g., a first sensor array), a sensor array 410b (e.g., a second sensor array), and a sensor array 410c (e.g., a first sensor array). Each of the sensor arrays 410 are adjacent to the second surface 404 and include a plurality of the back sensors 210. For example, the sensor array 410a includes an exterior sensor 408a (e.g., a first exterior sensor), the sensor array 410b includes an exterior sensor 408b (e.g., a second back sensor), and the sensor array 410c includes an exterior sensor 408c (e.g., a third back sensor). While the reference sensors are positioned along the interior surface and the sensor matrix is positioned along to the exterior surface in FIG. 4, in other examples the reference sensors are positioned along the exterior surface and the sensor matrix is positioned along to the interior surface.

In the illustrated example, the cabin sensors 406 and the exterior sensors 408 collect ambient light measurements to enable the opaqueness detector 122 to detect whether condensation, rain droplets, snow, ice, dirt and/or other opaque materials have collected on the windshield 102. The opaqueness detector 122 compares ambient light measurements collected by the cabin sensors 406 to ambient light measurements collected by the exterior sensors 408 to determine whether opaque material has collected on the front surface 204 of the side mirror 108a.

For example, the first cabin sensor 406a collects an ambient light intensity (e.g., a first ambient light intensity) and the exterior sensor 408a collects an ambient light intensity (e.g., a second ambient light intensity). The opaqueness detector 122 compares the first ambient light intensity and the second ambient light intensity to determine whether condensation and/or other opaque material has collected on the windshield 102 near the exterior sensor 408a. For example, the opaqueness detector 122 detects that condensation has formed on the windshield 102 near the exterior sensor 408a when the second ambient light intensity is less than the first ambient light intensity by a first predetermined value that corresponds to a layer of condensation on the windshield 102. Further, a second cabin sensor collects an ambient light intensity (e.g., a third ambient light intensity) that the opaqueness detector 122 utilizes to detect whether condensation and/or other opaque material has collected on the windshield 102 by comparing the first ambient light intensity to the third ambient light intensity.

Additionally or alternatively, the opaqueness detection assembly 400 enables the opaqueness detector 122 to determine which type of material has formed an opaque surface on the windshield 102. For example, when the second ambient light intensity is less than the first ambient light intensity by a second predetermined value, the opaqueness detector 122 detects that rain droplets are on the windshield 102 near the exterior sensor 408a. When the second ambient light intensity is less than the first ambient light intensity by a third predetermined value, the opaqueness detector 122 detects that snow is on the windshield 102 near the exterior sensor 408a. Further, when the second ambient light intensity is less than the first ambient light intensity by a fourth predetermined value, the opaqueness detector 122 detects that ice is on the windshield 102 near the exterior sensor 408a.

The opaqueness detection assembly 400 of the illustrated example also enables the opaqueness detector 122 to determine a location of opaque material on the windshield 102. For example, the cabin sensors 406 and the exterior sensors 408 of the sensor arrays 410 are utilized to determine which portion of the windshield 102 is covered by the opaque material 202.

In the illustrated example, the cabin sensors 406 are coupled to the first surface 402, and the exterior sensors 408 are coupled to the second surface 404 to securely position the cabin sensors 406 and the exterior sensors 408. Further, the cabin sensors 406 and the exterior sensors 408 are coupled to the first surface 402 and the second surface 404, respectively, to prevent material from being positioned between the cabin sensors 406 and/or the exterior sensors 408 and the windshield 102. In the illustrated example, the cabin sensors 406 and the exterior sensors 408 may be coupled to the windshield 102 via a bracket and/or adhesive. Further, in the illustrated example, the exterior sensors 408 of the sensor array 410c are embedded into the windshield 102 such that the exterior sensors 408 of the sensor array 410c and the windshield 102 form a flat surface 412. In other examples, more (e.g., all) or less of the exterior sensors 408 and/or one or more of the cabin sensors 406 may be embedded into the windshield 102 to form a flat surface (e.g., the flat surface 412). Further, in other examples, the front sensors 206 may be spaced apart from the front surface 204 and/or the back sensors 210 may be spaced apart from the back surface 306.

Figure 5:
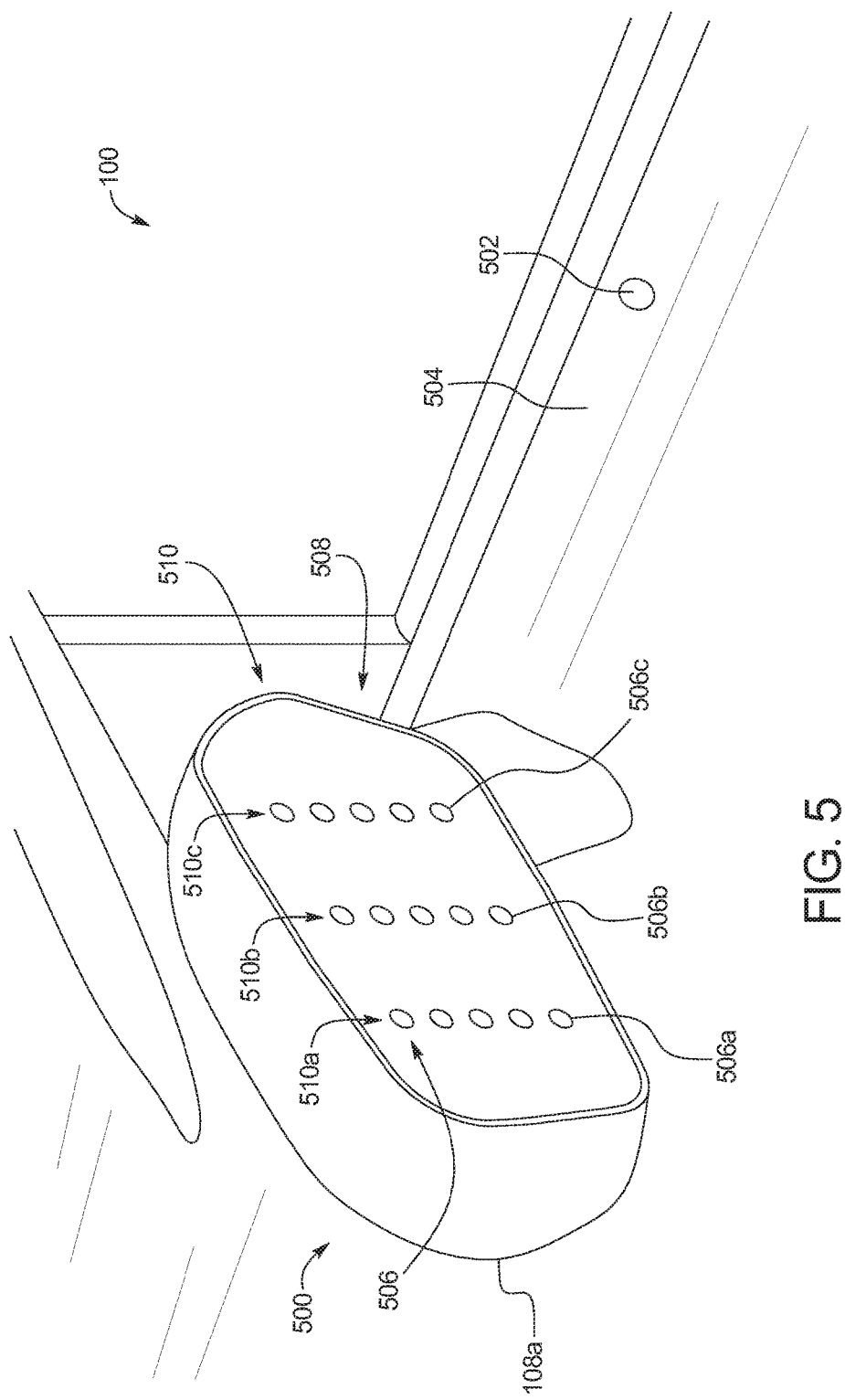
FIG. 5 illustrates a side window and a door of the vehicle of FIG. 1 and another example opaqueness detection assembly in accordance with the teachings disclosed herein.
Figure 6:
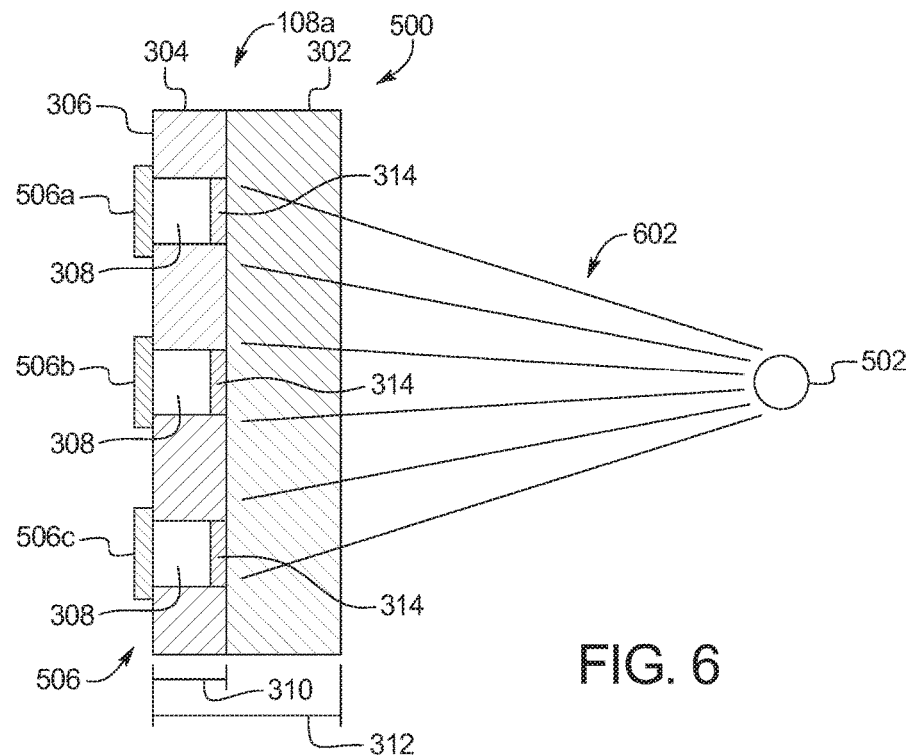
FIG. 6 depicts a cross-sectional diagram of the side window and the opaqueness detection assembly of FIG. 5.

FIG. 5 illustrates an example opaqueness detection assembly 500 (e.g., the opaqueness detection assembly 124) that is utilized to detect whether opaque material has collected on or formed in the front surface 204 of the side mirror 108a in accordance with the teachings disclosed herein. The side mirror 108a is discussed in detail with respect to FIGS. 2 and 3. Because the side mirror 108a of FIGS. 5 and 6 is identical or substantially similar to the side mirror 108a of FIGS. 2 and 3, some features of the side mirror 108a will not be discussed in further detail below. Further, the opaqueness detection assembly 200 may be utilized for detecting opaqueness of the side mirror 108b. Because the side mirror 108b is identical or substantially similar to the side mirror 108a, some features of the side mirror 108b will not be discussed in further detail below.

As illustrated in FIG. 5, the opaqueness detection assembly 500 includes a light transmitter 502 (e.g., an LED transmitter, an infrared transmitter, etc.) adjacent to and spaced apart from the front surface 204 of the side mirror 108a. In the illustrated example, the light transmitter 502 is coupled to a door 504 of the vehicle 100 near the side mirror 108a. In other examples, the light transmitter 502 is coupled to another surface of the vehicle 100 that is near the side mirror 108a.

Further, the opaqueness detection assembly 500 of the illustrated example includes a plurality of light sensors 506 (e.g., LED receivers, infrared receivers, etc.) adjacent to the back surface 306 of the side mirror 108a such that the side mirror 108a is positioned between the light transmitter 502 and the light sensors 506. In the illustrated example, the light sensors 506 form a sensor matrix 508 that includes a plurality of sensor arrays 510. The sensor arrays 510 include a sensor array 510a (e.g., a first sensor array), a sensor array 510b (e.g., a second sensor array), and a sensor array 510c (e.g., a first sensor array). Each of the sensor arrays 214 are adjacent to the back surface 306 of the side mirror 108a and include a plurality of the light sensors 506. For example, the sensor array 510a includes a first light sensor (e.g., a light sensor 506a of FIG. 6), the sensor array 510b includes a second light sensor (e.g., a light sensor 506b of FIG. 6), and the sensor array 510c includes a third light sensor (e.g., a light sensor 506c of FIG. 6).

In the illustrated example, the light transmitter 502 emits a light beam (e.g., a light beam 602 of FIG. 6) toward the side mirror 108a and the light sensors 506 detect light intensities of the light beam. The opaqueness detector 122 determines whether opaque material (e.g., condensation, rain droplets, snow, ice, a cracked surface) has collected on and/or formed in the side mirror 108a based on the light intensities measured by the light sensors 506. For example, the opaqueness detector 122 determines whether condensation is on the side mirror 108a based on the light intensity (e.g., a first light intensity) measured by the light sensor 506a (e.g., a first light sensor). In some examples, the light beam is a focused light beam that is directed to one of the light sensors 506 (e.g., the first light sensor) to enable that one of the light sensors 506 to receive the light beam and, thus, to detect the light intensity of the light beam. In other examples, the light beam is an unfocused light beam that is directed toward the side mirror 108a such that more than one of the light sensors 506 (e.g., each of the light sensors 506 of the sensor matrix 508 and/or one or more of the sensor arrays 510) are able to receive the light beam and, thus, detect the light intensity of the light beam.

In some examples, the opaqueness detection assembly 500 enables the opaqueness detector 122 to determine which type of material is forming an opaque surface on the side mirror 108a. For example, when the light intensity (e.g., the first light intensity) measured by the light sensor 506a (e.g., the first light sensor) is less than a reference light intensity associated with a non-opaque mirror, the opaqueness detector 122 detects that condensation is on the side mirror 108a near the light sensor 506a. When the first light intensity is less than the reference light intensity by a second predetermined value, the opaqueness detector 122 detects that rain droplets are on the side mirror 108a near the light sensor 506a. When the first light intensity is less than the reference light intensity by a third predetermined value, the opaqueness detector 122 detects that snow is on the side mirror 108a near the light sensor 506a. Further, when the first light intensity is less than the reference light intensity by a fourth predetermined value, the opaqueness detector 122 detects that ice is on the side mirror 108a near the light sensor 506a.

The opaqueness detection assembly 500 of the illustrated example also enables the opaqueness detector 122 to determine a location of opaque material on the side mirror 108a. The light sensors 506 of the sensor matrix 508 and/or the sensor arrays 510 are utilized to determine a location of opaque material on the side mirror 108a by enabling the opaqueness detector 122 to identify which of the light sensors 506 collect light intensity that is affected by the opaque material and which of the light sensors 506 collect light intensity that is not affected by the opaque material. For example, each of the light sensors 506 detects a respective light intensity of the light beam, and the opaqueness detector 122 determines the location of the opaque material based upon the respective light intensities of the light sensors 506.

FIG. 6 depicts a cross-sectional diagram of the side mirror 108a and the opaqueness detection assembly 500. The light sensors 506 are coupled to the back surface 306 of the side mirror 108a to securely position the light sensors 506. In the illustrated example, the light sensors 506 are coupled to the back surface 306 to prevent material from being positioned between the light sensors 506 and the side mirror 108a that potentially may otherwise affect light intensity measurements collected by the light sensors 506. For example, the light sensors 506 are coupled to the side mirror 108a via a bracket and/or adhesive. In other examples, the light sensors 506 may be spaced apart from the back surface 306.

As illustrated in FIG. 6, the light transmitter 502 emits a light beam 602 toward the side mirror 108a to enable one or more of the light sensors 506 to collect a light intensity measurement of the light beam 602. In the illustrated example, the light beam 602 is an unfocused light beam that directs light to more than one of the light sensors 506. For example, the light beam 602 is directed to each of the light sensors 506 to enable each of the light sensors 506 to collect a light intensity measurement of the light beam 602. By enabling each of the light sensors 506 to collect a light intensity measurement, the light beam 602 that is unfocused enables the opaqueness detector 122 to determine a location of opaque material on side mirror 108a by identifying which of light sensors 506 of the sensor matrix 508 and/or the sensor arrays 510 detect a reduced light intensity. Further, in the illustrated example, the light transmitter 502 is an LED transmitter and the light beam 602 that is unfocused is a scatter beam. In other examples, the light transmitter 502 is a laser transmitter and the light beam 602 that is unfocused is a Gaussian beam.

The side mirror 108a of the illustrated example includes the apertures 308 that extend through the thickness 310 of the reflective layer 304 such that the apertures 308 extend through at least a portion of the thickness 312 of the side mirror 108a. Each of the light sensors 506 (e.g., the light sensor 506a, the light sensor 506b, the light sensor 506c) is adjacent to a corresponding one of the apertures 308 to enable each of the light sensors 506 to receive the light beam 602 and collect a measurement of light intensity (e.g., the first light intensity) of the light beam 602. Further, in the illustrated example, each of the apertures 308 is covered with the electrochromic material layer 314 to camouflage the apertures 308 with the front surface 204 of the side mirror 108a.

Figure 7:
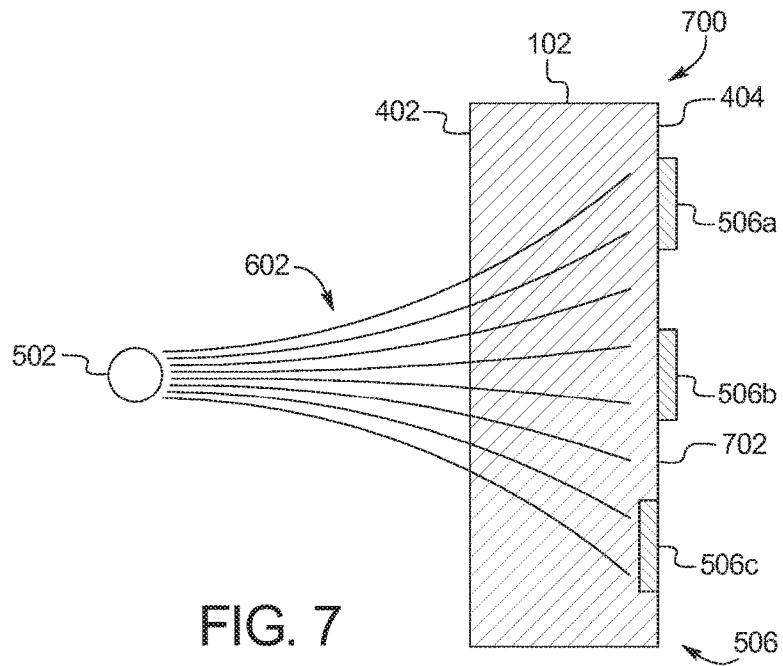
FIG. 7 depicts a cross-sectional diagram of a window of the vehicle of FIG. 1 and the opaqueness detection assembly of FIG. 5.

FIG. 7 depicts a cross-sectional diagram of an opaqueness detection assembly 700 that facilitates detection of opaque materials located on and/or formed in a window of the vehicle 100. In the illustrated example, the opaqueness detection assembly 700 (e.g., the opaqueness detection assembly 126) is utilized to monitor the windshield 102. Additionally or alternatively, the opaqueness detection assembly 700 is utilized to monitor one or more of the side windows 106 and/or the rearview window 104 of the vehicle 100.

The opaqueness detection assembly 700 of the illustrated example includes the light transmitter 502 and the light sensors 506 that are identical and/or substantially similar to those components of the opaqueness detection assembly 500. Because the light transmitter 502 and the light sensors 506 have been described with respect to FIGS. 5 and 6, some features of those components are not described in further detail below. Further, features of the windshield 102 are discussed in detail with respect to FIG. 4. Because the windshield 102 of FIG. 7 is identical or substantially similar to the windshield 102 of FIG. 4, some features of the windshield 102 will not be discussed in further detail below.

As illustrated in FIG. 7, the windshield 102 is positioned between the light transmitter 502 and the light sensors 506 (e.g., including the light sensor 506a). In the illustrated example, the light transmitter 502 is adjacent to and spaced apart from the first surface 402 (e.g., the interior surface) of the windshield 102, and the light sensors 506 are adjacent to the second surface 404 (e.g., the exterior surface) of the windshield 102. For example, the light transmitter 502 is coupled to an interior surface of the vehicle 100 (e.g., an upper surface of a dashboard) and the light sensors 506 are coupled to the second surface 404 of the windshield 102. In other examples, the light transmitter 502 is adjacent to the first surface 402, and the sensor matrix 508 adjacent to the second surface 404.

The light transmitter 502 emits the light beam 602 toward the windshield 102 to enable one or more of the light sensors 506 to collect a light intensity measurement of the light beam 602. In the illustrated example, the light beam 602 is an unfocused light beam that directs light to more than one of the light sensors 506. For example, the light beam 602 is directed to each of the light sensors 506 to enable each of the light sensors 506 to collect a light intensity measurement of the light beam 602. Each of the light sensors 506 collect a light intensity measurement to enable the opaqueness detector 122 to determine a location of opaque material on windshield 102 by identifying which of light sensors 506 detect a reduced light intensity. Further, in the illustrated example, the light transmitter 502 is a laser transmitter and the light beam 602 that is unfocused is a Gaussian beam. In other examples, the light transmitter 502 is an LED transmitter and the light beam 602 that is unfocused is a scatter beam.

The opaqueness detector 122 determines whether opaque material (e.g., condensation, rain droplets, snow, ice, a cracked surface) is on the windshield 102 based on the light intensities measured by the light sensors 506. For example, the opaqueness detector 122 determines whether condensation is on the windshield 102 based on the light intensity (e.g., a first light intensity) measured by the light sensor 506a (e.g., a first light sensor).

Further, the opaqueness detection assembly 700 enables the opaqueness detector 122 to determine which type of material has formed an opaque surface on the windshield 102. For example, when the light intensity (e.g., the first light intensity) measured by the light sensor 506a (e.g., the first light sensor) is less than a reference light intensity associated with a non-opaque windshield, the opaqueness detector 122 detects that condensation is on the windshield 102 near the light sensor 506a. When the first light intensity is less than the reference light intensity by a second predetermined value, the opaqueness detector 122 detects that rain droplets are on the windshield 102 near the light sensor 506a. When the first light intensity is less than the reference light intensity by a third predetermined value, the opaqueness detector 122 detects that snow is on the windshield 102 near the light sensor 506a. Further, when the first light intensity is less than the reference light intensity by a fourth predetermined value, the opaqueness detector 122 detects that ice is on the windshield 102 near the light sensor 506a.

Further, in the illustrated example, the light sensors 506 of the sensor array 510c are embedded into the windshield 102 such that the light sensors 506 of the sensor array 510c and the windshield 102 form a flat surface 702. In other examples, more (e.g., all) or less of the light sensors 506 may be embedded into the windshield 102 to form a flat surface (e.g., the flat surface 702).

Figure 8:
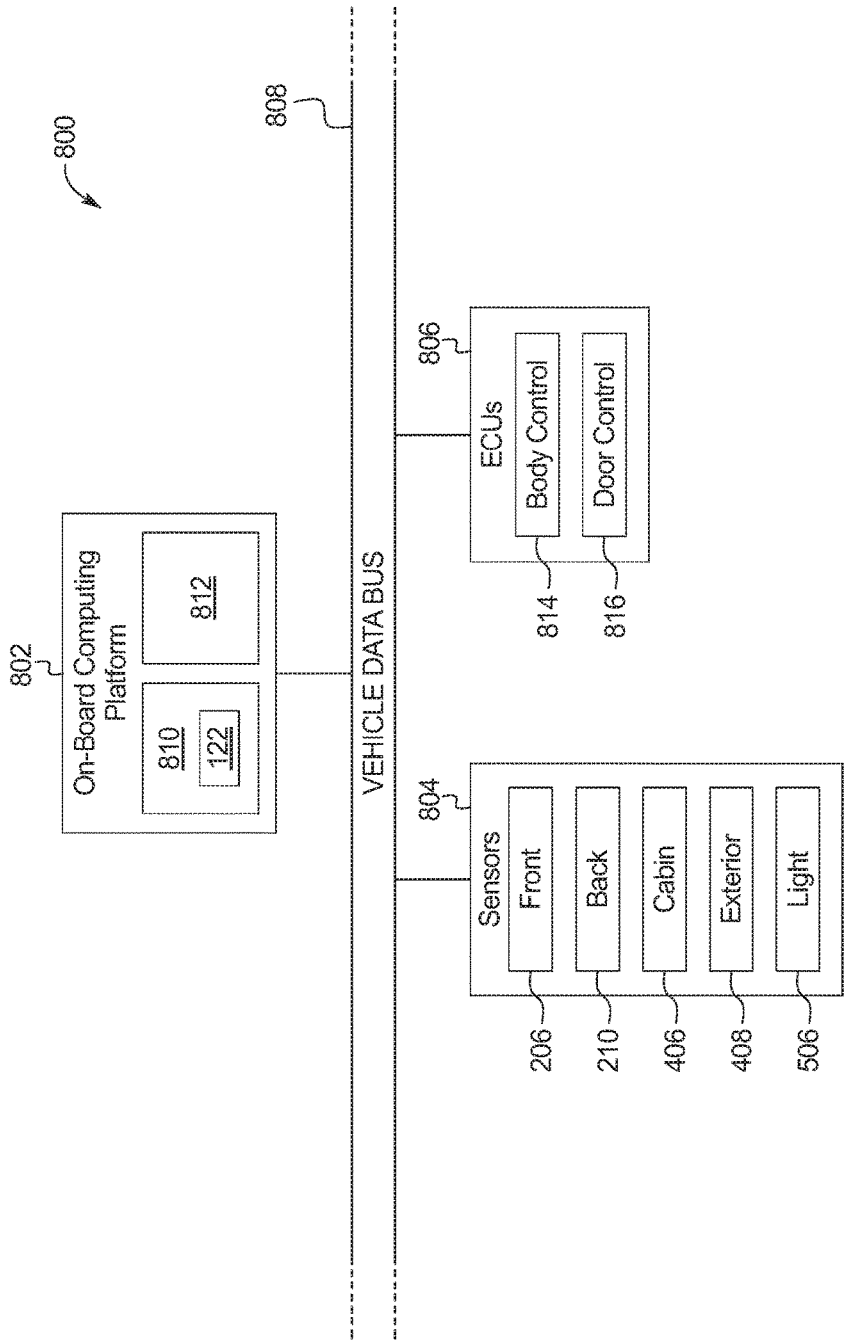
FIG. 8 is a block diagram of electronic components of the vehicle of FIG. 1.

FIG. 8 is a block diagram of electronic components 800 of the vehicle 100. As illustrated in FIG. 8, the electronic components 800 include an on-board computing platform 802, sensors, electronic control units (ECUs) 806, and a vehicle data bus 808.

The on-board computing platform 802 includes a microcontroller unit, controller or processor 810 and memory 812. In some examples, the processor 810 of the on-board computing platform 802 is structured to include the opaqueness detector 122. Alternatively, in some examples, the opaqueness detector 122 is incorporated into another electronic control unit (ECU) with its own processor 810 and memory 812. The processor 810 may be any suitable processing device or set of processing devices such as, but not limited to, a microprocessor, a microcontroller-based platform, an integrated circuit, one or more field programmable gate arrays (FPGAs), and/or one or more application-specific integrated circuits (ASICs). The memory 812 may be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc). In some examples, the memory 812 includes multiple kinds of memory, particularly volatile memory and non-volatile memory.

The memory 812 is computer readable media on which one or more sets of instructions, such as the software for operating the methods of the present disclosure, can be embedded. The instructions may embody one or more of the methods or logic as described herein. For example, the instructions reside completely, or at least partially, within any one or more of the memory 812, the computer readable medium, and/or within the processor 810 during execution of the instructions.

The terms "non-transitory computer-readable medium" and "computer-readable medium" include a single medium or multiple media, such as a centralized or distributed database, and/or associated caches and servers that store one or more sets of instructions. Further, the terms "non-transitory computer-readable medium" and "computer-readable medium" include any tangible medium that is capable of storing, encoding or carrying a set of instructions for execution by a processor or that cause a system to perform any one or more of the methods or operations disclosed herein. As used herein, the term "computer readable medium" is expressly defined to include any type of computer readable storage device and/or storage disk and to exclude propagating signals.

The sensors 804 are arranged in and around the vehicle 100 to monitor properties of the vehicle 100 and/or an environment in which the vehicle 100 is located. One or more of the sensors 804 may be mounted to measure properties around an exterior of the vehicle 100. Additionally or alternatively, one or more of the sensors 804 may be mounted inside a cabin of the vehicle 100 or in a body of the vehicle 100 (e.g., an engine compartment, wheel wells, etc.) to measure properties in an interior of the vehicle 100. For example, the sensors 804 include accelerometers, odometers, tachometers, pitch and yaw sensors, wheel speed sensors, microphones, tire pressure sensors, biometric sensors and/or sensors of any other suitable type. In the illustrated example, the sensors 804 include the front sensors 206 and the back sensors 210 of the opaqueness detection assembly 200, the cabin sensors 406 and the exterior sensors 408 of the opaqueness detection assembly 400, and the light sensors 506 of the opaqueness detection assembly 500 and/or the opaqueness detection assembly 700.

The ECUs 806 monitor and control the subsystems of the vehicle 100. For example, the ECUs 806 are discrete sets of electronics that include their own circuit(s) (e.g., integrated circuits, microprocessors, memory, storage, etc.) and firmware, sensors, actuators, and/or mounting hardware. The ECUs 806 communicate and exchange information via a vehicle data bus (e.g., the vehicle data bus 808). Additionally, the ECUs 806 may communicate properties (e.g., status of the ECUs 806, sensor readings, control state, error and diagnostic codes, etc.) to and/or receive requests from each other. For example, the vehicle 100 may have seventy or more of the ECUs 806 that are positioned in various locations around the vehicle 100 and are communicatively coupled by the vehicle data bus 808.

In the illustrated example, the ECUs 806 include a body control module 814 and a door control unit 816. For example, the body control module 814 controls one or more subsystems throughout the vehicle 100, such as an immobilizer system, the HVAC system 114, etc. For example, the body control module 814 includes circuits that drive one or more of relays (e.g., to control wiper fluid, etc.), brushed direct current (DC) motors (e.g., to control wipers, etc.), stepper motors, LEDs, etc. The door control unit 816 controls one or more electrical systems located on doors (e.g., the door 504 of FIG. 5) of the vehicle 100, such as power windows, power locks, power mirrors, the mirror heating elements 220, etc. For example, the door control unit 816 includes circuits that drive one or more of relays brushed direct current (DC) motors (e.g., to control power seats, power locks, power windows, etc.), stepper motors, LEDs, etc.

The vehicle data bus 808 communicatively couples the on-board computing platform 802, the sensors 804, and the ECUs 806. In some examples, the vehicle data bus 808 includes one or more data buses. The vehicle data bus 808 may be implemented in accordance with a controller area network (CAN) bus protocol as defined by International Standards Organization (ISO) 11898-1, a Media Oriented Systems Transport (MOST) bus protocol, a CAN flexible data (CAN-FD) bus protocol (ISO 11898-7) and/a K-line bus protocol (ISO 9141 and ISO 14230-1), and/or an Ethernet™ bus protocol IEEE 802.3 (2002 onwards), etc.

Figure 9:
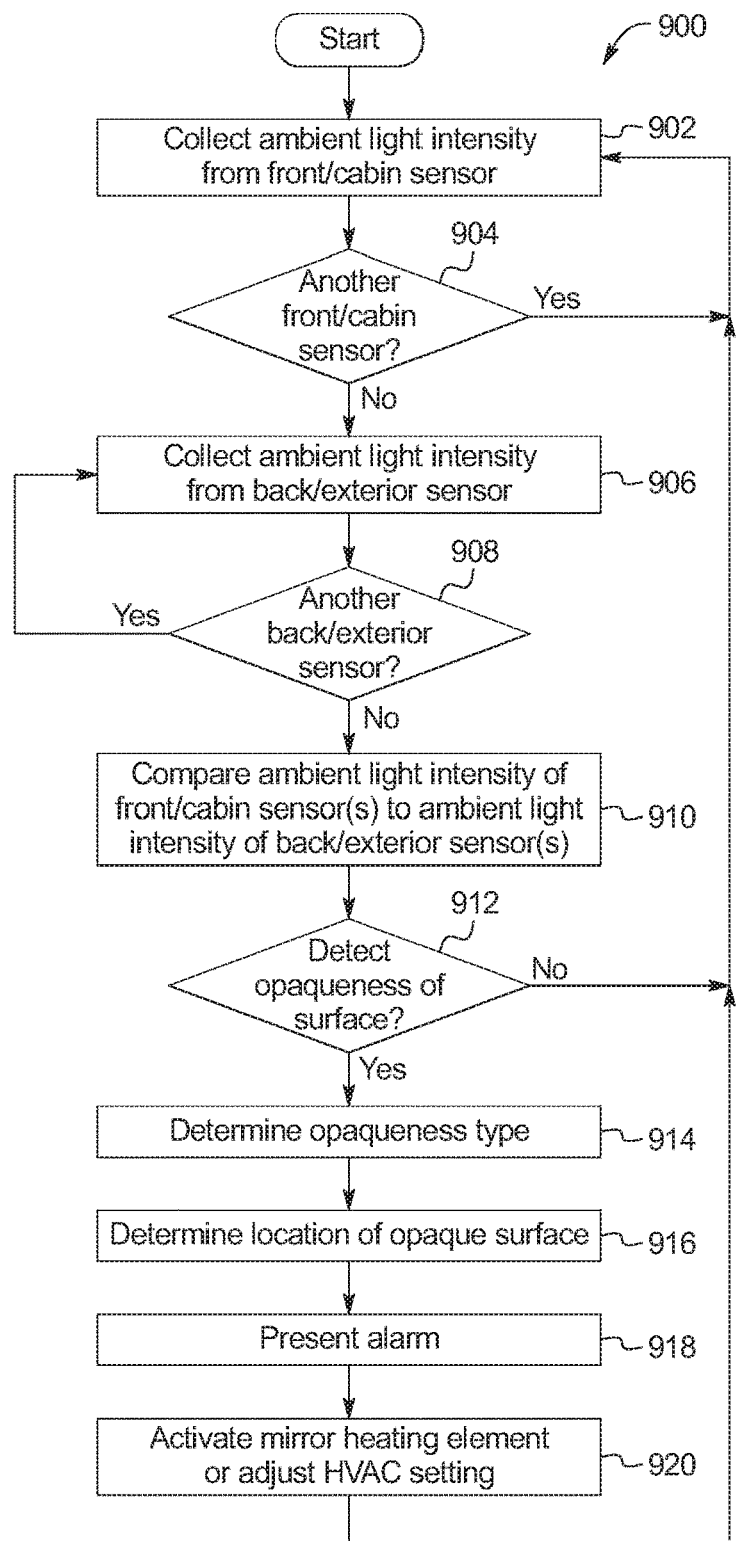
FIG. 9 is a flowchart for detecting condensation on a vehicle surface via the opaqueness detection assembly of FIGS. 2-4 in accordance with the teachings disclosed herein.

FIG. 9 is a flowchart of an example method 900 to detect condensation on a vehicle surface via an opaqueness detection assembly. The flowchart of FIG. 9 is representative of machine readable instructions that are stored in memory (such as the memory 812 of FIG. 8) and include one or more programs which, when executed by a processor (such as the processor 810 of FIG. 8), cause the vehicle 100 to implement the example opaqueness detector 122 of FIGS. 1 and 8. While the example program is described with reference to the flowchart illustrated in FIG. 9, many other methods of implementing the example opaqueness detector 122 may alternatively be used. For example, the order of execution of the blocks may be rearranged, changed, eliminated, and/or combined to perform the method 900. Further, because the method 900 is disclosed in connection with the components of FIGS. 1-4 and 8, some functions of those components will not be described in detail below.

For examples in which the vehicle surface is a mirror (e.g., one of the side mirrors 108, the rearview mirror 110), the method 900 begins at block 902 at which the opaqueness detector 122 collects an ambient light intensity (e.g., a first ambient intensity) via one of the front sensors 206 (e.g., the front sensor 206a). At block 904, the opaqueness detector 122 determines whether there is another of the front sensors 206 from which to collect another ambient light intensity. In response to the opaqueness detector 122 determining that there is another of the front sensors 206 (e.g., the front sensor 206b), the method 900 repeats blocks 902, 904. Otherwise, in response to the opaqueness detector 122 determining that there is not another of the front sensors 206, the method 900 proceeds to block 906 at which the opaqueness detector 122 collects an ambient light intensity (e.g., a second ambient intensity) via one of the back sensors 210 (e.g., the back sensor 210a). At block 908, the opaqueness detector 122 determines whether there is another of the back sensors 210 from which to collect another ambient light intensity. In response to the opaqueness detector 122 determining that there is another of the back sensors 210 (e.g., the back sensor 210b), the method 900 repeats blocks 906, 908. Otherwise, in response to the opaqueness detector 122 determining that there is not another of the back sensors 210, the method 900 proceeds to block 910 at which the opaqueness detector 122 compares the ambient light intensity collected from the front sensors 206 to the ambient light intensity collected from the back sensors 210.

Similarly, for examples in which the vehicle surface is a window (e.g., the windshield 102, the rearview window 104, one of the side windows 106), the method 900 begins at block 902 at which the opaqueness detector 122 collects an ambient light intensity (e.g., a first ambient intensity) via one of the cabin sensors 406 (e.g., the first cabin sensor 406*a*). At block 904, the opaqueness detector 122 determines whether there is another of the cabin sensors 406 from which to collect another ambient light intensity. In response to the opaqueness detector 122 determining that there is another of the cabin sensors 406, the method 900 repeats blocks 902, 904. Otherwise, in response to the opaqueness detector 122 determining that there is not another of the cabin sensors 406, the method 900 proceeds to block 906 at which the opaqueness detector 122 collects an ambient light intensity (e.g., a second ambient intensity) via one of the exterior sensors 408 (e.g., the exterior sensor 408*a*). At block 908, the opaqueness detector 122 determines whether there is another of the exterior sensors 408 from which to collect another ambient light intensity. In response to the opaqueness detector 122 determining that there is another of the exterior sensors 408 (e.g., the exterior sensor 408*b*), the method 900 repeats blocks 906, 908. Otherwise, in response to the opaqueness detector 122 determining that there is not another of the exterior sensors 408, the method 900 proceeds to block 910 at which the opaqueness detector 122 compares the ambient light intensity collected from the cabin sensors 406 to the ambient light intensity collected from the exterior sensors 408.

For examples in which the vehicle surface is a mirror or a window, the method proceeds to block 912 at which the opaqueness detector 122 detects whether the vehicle surface is opaque (e.g., due to condensation, rain droplets, ice, snow, cracking of the vehicle surface, etc.) based upon the comparison of the ambient light intensities performed at block 910. For example, the opaqueness detector 122 determines whether the ambient light intensity collected from one or more of the back sensors 210 or the exterior sensors 408 is less than the ambient light intensity collected from the front sensors 206 or the cabin sensors 406, respectively, by a predetermined value that is associated with a source of opaqueness.

In response to the opaqueness detector 122 detecting that the vehicle surface is not opaque, the method 900 returns to block 902. For example, the opaqueness detector 122 detects that the vehicle surface is not opaque (i.e., clear) when a difference between the ambient light intensity of the exterior sensors 408 is less than the ambient light intensity collected from the front sensors 206 or the cabin sensors 406, respectively, by a predetermined value (e.g., a fifth predetermined value) associated with a clear vehicle surface. In some examples, the predetermined value associated with the clear vehicle surface is zero. Otherwise, in response to the opaqueness detector 122 detecting that the vehicle surface is opaque, the method 900 proceeds to block 914.

At block 914, the opaqueness detector 122 determines a type of opaqueness that is detected on the vehicle surface. For example, the opaqueness detector 122 determines that condensation is on the vehicle surface in response to determining that the second ambient light intensity measured by one or more of the back sensors 210 or the exterior sensors 408 is less than the first ambient light intensity measured by one or more of the front sensors 206 or the cabin sensors 406, respectively, by a first predetermined value. The opaqueness detector 122 determines that rain droplets is on the vehicle surface in response to determining that the second ambient light intensity measured by one or more of the back sensors 210 or the exterior sensors 408 is less than the first ambient light intensity measured by one or more of the front sensors 206 or the cabin sensors 406, respectively, by a second predetermined value. The opaqueness detector 122 determines that snow is on the vehicle surface in response to determining that the second ambient light intensity measured by one or more of the back sensors 210 or the exterior sensors 408 is less than the first ambient light intensity measured by one or more of the front sensors 206 or the cabin sensors 406, respectively, by a third predetermined value. The opaqueness detector 122 determines that ice is on the vehicle surface in response to determining that the second ambient light intensity measured by one or more of the back sensors 210 or the exterior sensors 408 is less than the first ambient light intensity measured by one or more of the front sensors 206 or the cabin sensors 406, respectively, by a fourth predetermined value.

Further, at block 916, the opaqueness detector 122 detection a location (e.g., the location 218) of the opaque material on the vehicle surface by identifying which of the back sensors 210 or the exterior sensors 408 measured an ambient light intensity that is less than the front sensors 206 or the cabin sensors 406, respectively, by the predetermined value associated with the opaque material. At block 918, the opaqueness detector 122 presents an alarm to a driver of the vehicle 100 (e.g., via the display 118, the speakers 120, etc.) to alert the driver that at least a portion of the vehicle surface has become opaque. At block 920, the opaqueness detector 122 activates the mirror heating elements 220 in response to detecting that opaque material has collected on or formed in a mirror of the vehicle 100 and/or adjusts an HVAC setting of the HVAC system 114 in response to detecting that opaque material has collected on or formed in a window of the vehicle 100.

Figure 10:
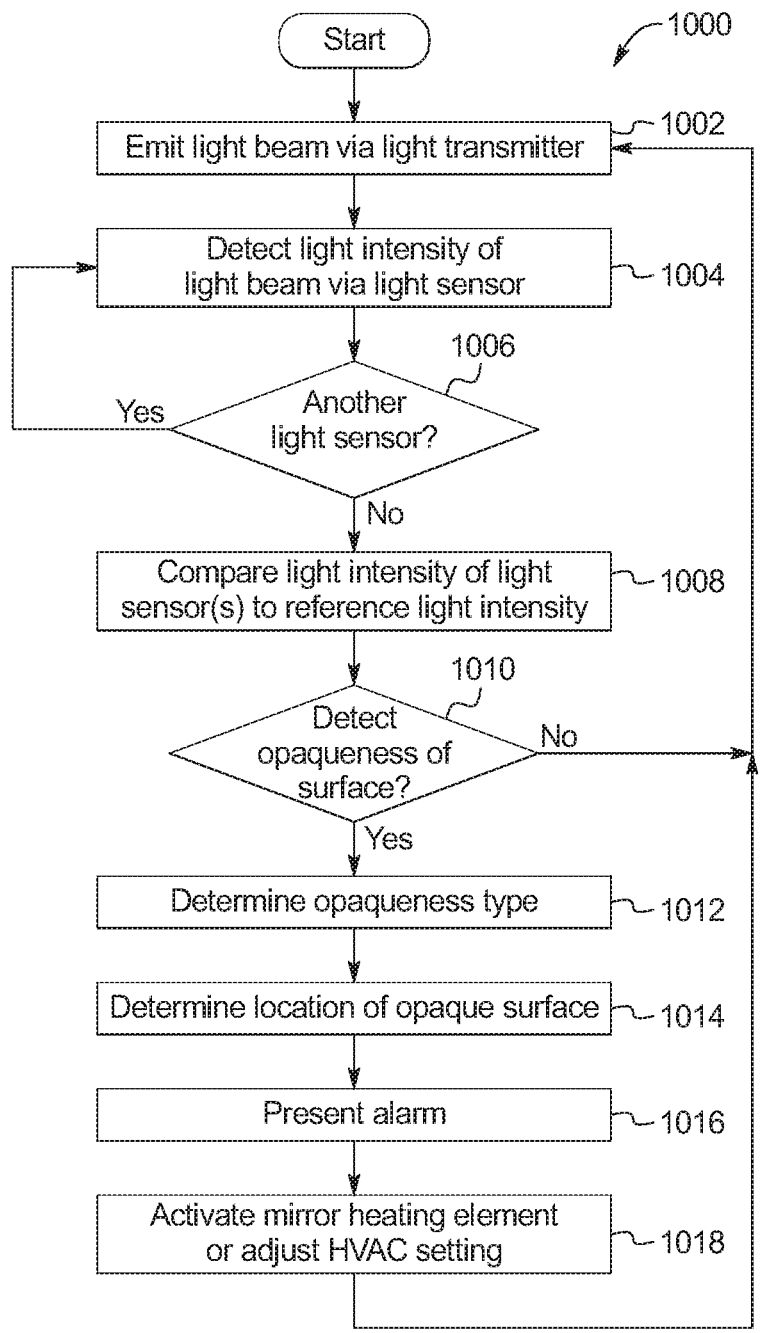
FIG. 10 is a flowchart for detecting condensation on a vehicle surface via the opaqueness detection assembly of FIGS. 5-7 in accordance with the teachings disclosed herein.

FIG. 10 is a flowchart of an example method 1000 to detect condensation on a vehicle surface via another opaqueness detection assembly. The flowchart of FIG. 10 is representative of machine readable instructions that are stored in memory (such as the memory 812 of FIG. 8) and include one or more programs which, when executed by a processor (such as the processor 810 of FIG. 8), cause the vehicle 100 to implement the example opaqueness detector 122 of FIGS. 1 and 8. While the example program is described with reference to the flowchart illustrated in FIG. 10, many other methods of implementing the example opaqueness detector 122 may alternatively be used. For example, the order of execution of the blocks may be rearranged, changed, eliminated, and/or combined to perform the method 1000. Further, because the method 1000 is disclosed in connection with the components of FIGS. 1 and 5-8, some functions of those components will not be described in detail below.

Initially, at block 1002, the opaqueness detector 122 the light transmitter 502 emits the light beam 602 toward a vehicle surface (e.g., the windshield 102, the rearview window 104, one or more of the side windows 106, one or more of the side mirrors 108, the rearview mirror 110). At block 1004, the opaqueness detector 122 collects a light intensity measurement (e.g., a first ambient intensity) via one of the light sensors 506 (e.g., the light sensor 506*a*). At block 1006, the opaqueness detector 122 determines whether there is another of the light sensors 506 from which to collect another light intensity measurement. In response to the opaqueness detector 122 determining that there is another of the light sensors 506 (e.g., the light sensor 506*b*), the method 1000 repeats blocks 1004, 1006. Otherwise, in response to the opaqueness detector 122 determining that there is not another of the light sensors 506, the method 1000 proceeds to block 1008 at which the opaqueness detector 122 compares the light intensity measurement(s) collected from the front sensors 206 to a reference light intensity that corresponds to a non-opaque vehicle surface.

At block 1010, the opaqueness detector 122 detects whether the vehicle surface is opaque (e.g., due to condensation, rain droplets, ice, snow, cracking of the vehicle surface, etc.) based upon the comparison to the reference light intensity performed at block 1008. For example, the opaqueness detector 122 determines whether the ambient light intensity collected from one or more of the light sensors 506 is less than the reference light intensity by a predetermined value that is associated with a source of opaqueness.

In response to the opaqueness detector 122 detecting that the vehicle surface is not opaque, the method 1000 returns to block 1002. For example, the opaqueness detector 122 detects that the vehicle surface is not opaque (i.e., clear) when a difference between the light intensity of one or more of the light sensors 506 is less than the reference light intensity by a predetermined value (e.g., a fifth predetermined value, a value of 0) associated with a clear vehicle surface. Otherwise, in response to the opaqueness detector 122 detecting that the vehicle surface is opaque, the method 1000 proceeds to block 1012.

At block 1012, the opaqueness detector 122 determines a type of opaqueness that is detected on the vehicle surface. For example, the opaqueness detector 122 determines that condensation is on the vehicle surface in response to determining that the ambient light intensity measured by one or more of the light sensors 506 is less than the reference light intensity by a first predetermined value. The opaqueness detector 122 determines that rain droplets is on the vehicle surface in response to determining that the ambient light intensity measured by one or more of the light sensors 506 is less than the reference light intensity by a second predetermined value. The opaqueness detector 122 determines that snow is on the vehicle surface in response to determining that the ambient light intensity measured by one or more of the light sensors 506 is less than the reference light intensity by a third predetermined value. The opaqueness detector 122 determines that ice is on the vehicle surface in response to determining that the ambient light intensity measured by one or more of the light sensors 506 is less than the reference light intensity by a fourth predetermined value.

Further, at block 1014, the opaqueness detector 122 detection a location of the opaque material on the vehicle surface by identifying which of the light sensors 506 measured a light intensity that is less than reference light intensity by the predetermined value associated with the opaque material. At block 1016, the opaqueness detector 122 presents an alarm to a driver of the vehicle 100 (e.g., via the display 118, the speakers 120, etc.) to alert the driver that at least a portion of the vehicle surface has become opaque. At block 1018, the opaqueness detector 122 activates the mirror heating elements 220 in response to detecting that opaque material has collected on or formed in a mirror of the vehicle 100 and/or adjusts an HVAC setting of the HVAC system 114 in response to detecting that opaque material has collected on or formed in a window of the vehicle 100.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

What is claimed is:

1. A vehicle comprising:
a side mirror including a front surface and a back surface;
a light transmitter coupled to a vehicle door adjacent to the side mirror for emitting a light beam toward the side mirror;
a first light sensor coupled to the back surface for detecting a first light intensity of the light beam; and
an opaqueness detector that determines whether condensation is on the side mirror based upon the first light intensity.

2. The vehicle of claim 1, wherein, in response to detecting the condensation on the side mirror, the opaqueness detector at least one of presents an alarm and activates a mirror heating element.

3. The vehicle of claim 1, wherein the side mirror is positioned between the light transmitter and the first light sensor.

4. The vehicle of claim 1, wherein the side mirror includes:
a glass layer defining the front surface of the side mirror; and
a reflective layer coupled to the glass layer and defining the back surface of the side mirror.

5. A vehicle comprising:
a side mirror comprising:
a front surface;
a back surface;
a glass layer defining the front surface of the side mirror; and
a reflective layer coupled to the glass layer and defining the back surface of the side mirror;
a light transmitter adjacent to the front surface for emitting a light beam toward the side mirror;
a first light sensor adjacent to the back surface for detecting a first light intensity of the light beam; and
an opaqueness detector that determines whether condensation is on the side mirror based upon the first light intensity, wherein the reflective layer defines an aperture extending through a thickness of the reflective layer and the first light sensor is adjacent to the aperture defined by the reflective layer to enable the first light sensor to receive the light beam emitted by the light transmitter.

6. The vehicle of claim 5, wherein the aperture is covered with an electrochromic material layer to camouflage the aperture of the side mirror.

7. The vehicle of claim 1, further including a sensor array adjacent to the back surface of the side mirror, the sensor array includes a plurality of light sensors including the first light sensor.

8. A vehicle comprising:
a side mirror including a front surface and a back surface;
a light transmitter adjacent to the front surface for emitting a light beam toward the side mirror;

a first light sensor coupled to the back surface for detecting a first light intensity of the light beam;
an opaqueness detector that determines whether condensation is on the side mirror based upon the first light intensity; and
a sensor array adjacent to the back surface of the side mirror, the sensor array includes a plurality of light sensors including the first light sensor,
wherein the side mirror includes apertures extending through at least a portion of a thickness of the side mirror, each of the plurality of light sensors is adjacent to a corresponding one of the apertures to enable each of the plurality of light sensors to receive the light beam.

9. The vehicle of claim 8, wherein the light beam emitted by the light transmitter is an unfocused beam to enable each of the plurality of light sensors of the sensor array to receive the light beam.

10. The vehicle of claim 9, wherein the light transmitter is a LED transmitter and the light beam is a scattered beam.

11. The vehicle of claim 9, wherein the light transmitter is a laser transmitter and the light beam is a Gaussian beam.

12. A vehicle comprising:
a side mirror including a front surface and a back surface;
a light transmitter adjacent to the front surface for emitting a light beam toward the side mirror;
a first light sensor adjacent to the back surface for detecting a first light intensity of the light beam;
an opaqueness detector that determines whether condensation is on the side mirror based upon the first light intensity; and
a sensor array adjacent to the back surface of the side mirror, the sensor array includes a plurality of light sensors including the first light sensor, wherein:
each of the plurality of light sensors of the sensor array detects a respective light intensity of the light beam; and
the opaqueness detector determines a location of the condensation on the side mirror based upon the respective light intensities.

13. The vehicle of claim 1, wherein the opaqueness detector determines that condensation is on the side mirror in response to determining that the first light intensity is less than a reference light intensity less than a first predetermined value.

14. A method for detecting condensation on vehicle mirrors, the method comprising:
emitting a light beam toward a side mirror of a vehicle via a light transmitter coupled to a vehicle door adjacent to a front surface of the side mirror;
detecting a first light intensity of the light beam via a first light sensor coupled to a back surface of the side mirror; and
determining, via a processor, whether condensation is on the side mirror based upon the first light intensity.

15. The method of claim 14, further including at least one of presenting an alarm and activating a mirror heating element in response to determining that the condensation is on the side mirror.

16. A method for detecting condensation on vehicle mirrors, the method comprising:
emitting a light beam toward a side mirror of a vehicle via a light transmitter adjacent a front surface of the side mirror;
detecting a first light intensity of the light beam via a first light sensor adjacent a back surface of the side mirror; and
determining, via a processor, whether condensation is on the side mirror based upon the first light intensity, wherein the first light sensor is adjacent an aperture defined by the side mirror to enable the first light sensor to receive the light beam and detect the first light intensity.

17. The method of claim 14, further including determining that the condensation is on the side mirror in response to determining that the first light intensity is less than a reference light intensity by a first predetermined value.

18. A method for detecting condensation on vehicle mirrors, the method comprising:
emitting a light beam toward a side mirror of a vehicle via a light transmitter adjacent a front surface of the side mirror;
detecting a first light intensity of the light beam via a first light sensor adjacent a back surface of the side mirror;
determining, via a processor, whether condensation is on the side mirror based upon the first light intensity;
determining that the condensation is on the side mirror in response to determining that the first light intensity is less than a reference light intensity by a first predetermined value;
determining that rain droplets are on the side mirror in response to determining that the first light intensity is less than the reference light intensity by a second predetermined value;
determining that snow is on the side mirror in response to determining that the first light intensity is less than the reference light intensity by a third predetermined value; and
determining that ice is on the side mirror in response to determining that the first light intensity is less than the reference light intensity by a fourth predetermined value.

19. A method for detecting condensation on vehicle mirrors, the method comprising:
emitting a light beam toward a side mirror of a vehicle via a light transmitter adjacent a front surface of the side mirror;
detecting a first light intensity of the light beam via a first light sensor adjacent a back surface of the side mirror;
determining, via a processor, whether condensation is on the side mirror based upon the first light intensity; and
determining, via a sensor array, a location of the condensation on the side mirror, wherein the sensor array includes the first light sensor and is adjacent the back surface of the side mirror.

* * * * *